United States Patent [19]

Walker et al.

US005739019A

[11] Patent Number: 5,739,019
[45] Date of Patent: Apr. 14, 1998

[54] METHOD OF ISOLATING AND PROPAGATING MICROORGANISMS AND VIRUSES

[76] Inventors: Harrell L. Walker, Rt. 1 Box 2070-4, Ruston, La. 71270; Christopher L. Patrick, Rt. 4 Box 335, Rayville, La. 71269

[21] Appl. No.: 758,296

[22] Filed: Dec. 3, 1996

Related U.S. Application Data

[63] Continuation of Ser. No. 287,620, Aug. 8, 1994, abandoned.

[51] Int. Cl.⁶ .................. A01N 63/00; C12N 11/00; C12N 11/16; C12D 1/04
[52] U.S. Cl. .......... 435/174; 210/601; 210/615; 424/93.4; 424/93.6; 435/30; 435/34; 435/243; 435/235.1; 435/252.1; 435/254.1; 435/822; 435/261; 435/262
[58] Field of Search ............... 435/243, 34, 30, 435/174, 261, 235.1, 252.1, 254.1, 262, 822; 424/93.4, 93.6; 210/601, 615

[56] References Cited

U.S. PATENT DOCUMENTS

| | | | |
|---|---|---|---|
| 3,541,203 | 11/1970 | Fogle et al. | 424/17 |
| 3,975,520 | 8/1976 | Chain et al. | 424/181 |
| 4,464,474 | 8/1984 | Coursaget et al. | 436/513 |
| 4,643,968 | 2/1987 | Weaver | 435/32 |
| 4,718,935 | 1/1988 | Walker et al. | 71/79 |
| 4,767,441 | 8/1988 | Walker et al. | 71/79 |
| 4,791,063 | 12/1988 | Hou et al. | 435/243 |
| 4,818,530 | 4/1989 | Marois et al. | 424/93 |
| 4,859,597 | 8/1989 | Yang et al. | 435/239 |
| 4,879,232 | 11/1989 | MacDonald et al. | 435/179 |
| 4,921,803 | 5/1990 | Nohr | 435/179 |
| 4,950,600 | 8/1990 | Tanaka et al. | 435/178 |
| 4,950,601 | 8/1990 | MacDonald et al. | 435/179 |
| 4,959,301 | 9/1990 | Weaver et al. | 435/5 |
| 5,023,182 | 6/1991 | Vail | 435/235.1 |
| 5,055,390 | 10/1991 | Weaver et al. | 425/29 |
| 5,225,332 | 7/1993 | Weaver et al. | 435/29 |

FOREIGN PATENT DOCUMENTS

| | | |
|---|---|---|
| 2693474 | 1/1994 | France . |
| 36404009 | 2/1989 | Japan . |
| 3128988 | 5/1991 | Japan . |
| 0532621 | 10/1976 | U.S.S.R. . |
| 2159537 | 12/1985 | United Kingdom . |

OTHER PUBLICATIONS

"Virology", Dulbecco et al., Sep. 1988, pp. 29 & 65–66.

*Primary Examiner*—David M. Naff
*Assistant Examiner*—Deborah K. Ware
*Attorney, Agent, or Firm*—John M. Harrison; Randall C. Brown; Rick Matos

[57] ABSTRACT

A method of isolating microorganisms and viruses, including phages, bacteriophages and cyanophages from an environment, particularly an aquatic environment, and propagating the isolated microorganisms or viruses for inoculum formulation. A specific target organism or selective growth medium is first immobilized in a stable substrate form such as sodium alginate gel pellets. The substrate containing the target organism or growth medium is then introduced into the environment to be sampled and microorganisms and/or viruses which are pathogenic to the immobilized target organism, or which can utilize the nutrient included in the growth medium, colonize the pellets. The colonizing microorganism or viral pathogens are removed from the gel pellets using standard laboratory techniques. One of the isolated pathogens, particularly an isolated viral pathogen, may be selected and propagated for inoculum formulation. This is accomplished by immobilizing a concentrated suspension of host cells, such as a host cyanobacterium, in alginate gel pellets. When the immobilized host cells are inoculated with the selected pathogen, the concentrated suspension of host cells then supports production of high concentrations of the pathogen in the gel pellets. The pellets containing the pathogens can be easily harvested, used for storage of the pathogen, and/or formulated as inoculum.

10 Claims, No Drawings

METHOD OF ISOLATING AND PROPAGATING MICROORGANISMS AND VIRUSES

CROSS-REFERENCE TO RELATED APPLICATIONS

This is a continuation of U.S. application Ser. No. 08/287,620, filed on Aug. 8, 1994 which is now abandoned.

BACKGROUND OF THE INVENTION

1. Field of the Invention

This invention relates to methods of isolating microorganisms and viruses from an environment and propagating the isolated microorganisms and viruses and more particularly, to a method of isolating microorganisms and viruses, including phages, bacteriophages and cyanophages from a variety of environments, particularly an aquatic environment, and propagating the isolated microorganisms and viruses in a laboratory for inoculum formulation, for example. A selective growth medium or target organism is first immobilized in a stable substrate form such as sodium alginate gel pellets, which are then placed in a small bag typically constructed from nylon window screen. Typically, five to seven of the bags are placed in a sampling device characterized by a perforated PVC pipe having a sealed end and a cap threaded on the opposite end. The sampling device is suspended in a catfish pond or other body of water and after an appropriate time interval, typically two to seven days, the sampling device is retrieved and the gel pellets removed from each bag and placed in a Petri dish containing a culture of an appropriate host organism. Development of plaques in the culture indicates the presence of lytic agents such as bacteria, fungi or viruses, which are transferred from the plaques to other cultures of the host organism for propagation and evaluation. One of the isolated pathogens, particularly an isolated viral pathogen, may be selected and propagated for inoculum formulation. This is accomplished by immobilizing a concentrated suspension of host cells, such as a host cyanabacterium, in alginate gel pellets. When the immobilized host cells are inoculated with the selected pathogen, the concentrated suspension of host cells then supports production of high concentrations of the pathogen in the gel pellets. The pellets containing the pathogens can be easily harvested, used for storage of the pathogen and/or formulated as inoculum.

The isolation procedure utilized in this invention allows continuous sampling for microorganisms and/or viruses over an extended period of time and is thus more efficient than conventional microorganism and virus isolation or sampling methods, which are based on processing water samples collected during periodic sampling.

Off-flavor is one of the most serious problems in commercial production of channel catfish. There is convincing scientific evidence that compounds such as geosmin and 2-methylisoborneol (MIB) produced by certain species of cyanobacteria (blue-green algae) and actinomycetes, are responsible for much of this off-flavor. Viruses and microorganisms that are pathogenic or antagonistic to these cyanobacteria and actinomycetes occur naturally in the environment. Much potential exists to manipulate these pathogenic/antagonistic agents for safe and effective control of those cyanobacteria and actinomycetes that cause off-flavor.

2. Description of the Prior Art

Various techniques are known in the art for isolating microorganisms, viruses or virus particles from a host environment or for immobilizing microorganisms in a stable substrate form such as a gel. U.S. Pat. No. 4,464,474, dated Aug. 7, 1984, to Pierre L. J. Coursaget, describes a "Non-A, Non-B Hepatitis Assay and Vaccine", including a method of isolating a virus particle which is an etiological agent for NANB hepatitis from its host environment. U.S. Pat. No. 4,643,968, dated Feb. 17, 1987, to James C. Weaver, discloses a "Process For Determining Metabolism and Growth of Cells Under Various Conditions" by first suspending the cells in a liquid medium and then forming the liquid medium into small droplets which are caused to gel. My U.S. Pat. No. 4,718,935, dated Jan. 12, 1988, and U.S. Pat. No. 4,767,441, dated Aug. 30, 1988, details a "Method for the Preparation of Mycoherbicide-Containing Pellets", in which fungi are first selected and grown for a time sufficient to produce inoculum. The fungus cultures are harvested, homogenized and then diluted with sodium alginate in distilled water. Pelletization is then accomplished by dropwise addition of the sodium alginate mixture in $CaCl_2$. U.S. Pat. No. 4,791,063, dated Dec. 13, 1988, to Kenneth C. Hou, et al., discloses "Polyionene Transformed Modified Polysaccharide Supports" for removing microbial contaminants from biological liquids. The separation matrices defined by the polysaccharide supports exhibit antimicrobial activity and may be used as chromatographic separation media. U.S. Pat. No. 4,818,530, dated Apr. 4, 1989, to James J. Marois, describes "Preparation of Pellets Containing Fungi For Control of Soilborne Diseases", in which fungi are first selected and grown for a time sufficient to produce inoculum. The fungal propagules are then harvested, homogenized and diluted with sodium alginate solution. Pelletization is then accomplished by dropwise addition of the fungal propagule-alginate mixture into a solution of calcium chloride or calcium gluconate. U.S. Pat. No. 4,959,301, dated Sep. 25, 1990, to James C. Weaver, et al., details a "Process for Rapidly Enumerating Viable Entities" by measuring and analyzing microdroplets which contain viable biological entities. The viability of the biological entities is determined by measuring the growth of the biological entities initially contained in the microdroplets, by the appearance of colony-forming units or by using vital stains which are responsive to the biochemical activity and physical integrity of the biological entities. U.S. Pat. No. 5,055,390, dated Oct. 8, 1991, to James C. Weaver, et al., describes a "Process For Chemical Manipulation of Non-Aqueous Surrounded Microdroplets", in which a first set of microdroplets having an aqueous interior is surrounded by a non-aqueous fluid. The aqueous interior chemical composition of the first microdroplets is then manipulated by exposure to compounds soluble in both the non-aqueous and aqueous phases, or by contact with suspensions of a second set of microdroplets. U.S. Pat. No. 5,225,332, dated Jul. 6, 1993, to James C. Weaver, et al., details a "Process For Manipulation of Non-Aqueous Surrounded Microdroplets" involving formation of microdroplets and alteration of the position of the microdroplets using physical forces based on interactions of the microdroplets with a non-aqueous fluid surrounding the microdroplets.

SUMMARY OF THE INVENTION

The present invention is characterized by a method of isolating viruses and microorganisms from an environment, particularly an aquatic environment, and then propagating the isolated microorganisms and viruses in a laboratory for inoculum formulation. Isolation is accomplished by first immobilizing a target organism, such as a specific cyanobacterial organism or a selective growth medium, in a stable substrate form such as gel pellets produced from sodium alginate. The gel pellets containing the host organism or growth medium are then placed in a small nylon bag and a number of bags, typically from one to seven, is placed in a sampling device characterized by a polyvinylchloride tube having multiple openings or perforations, a sealed end and a cap threaded on the other end. The sampling device is suspended in a catfish pond or other aquatic environment for an appropriate time interval, usually from two to seven days, and then retrieved. The bags are removed from the sampling device and the gel pellets removed from the bags and plated on a culture of an appropriate host organism. Development of plaques in the culture indicates the presence of lytic agents such as bacteria, fungi or viruses, which are transferred from the plaques to other cultures of the host organism for propagation and evaluation. One of the isolated bacterial, fungal or viral pathogens may be selected and propagated for inoculum formulation by immobilizing a concentrated suspension of host cells, such as a host cyanobacterium, in alginate gel pellets. When the immobilized host cells are inoculated with the selected pathogen, the concentrated suspension of host cells then supports production of high concentrations of the pathogen in the gel pellets. The pellets containing the pathogens can be easily harvested, used for storage of the pathogen and/or formulated as inoculum.

Other uses for the method include isolating microorganisms which may colonize selective growth media, or degrade pesticides or other potential environmentally damaging compounds from soil. This can be accomplished by burying a perforated canister containing pellets of the compounds/selective growth media and removing microorganisms which have colonized the pellets, using standard laboratory techniques.

DESCRIPTION OF THE PREFERRED EMBODIMENTS

In accordance with the present invention, it has surprisingly been found that microorganisms and/or viruses having specific properties, such as tolerance to certain antibiotics or the capability of utilizing or decomposing specific substrates such as pesticides or other potential environmentally damaging compounds, can be isolated from a variety of different environments, including soil and aquatic environments, by immobilizing a target microorganism such as a specific cyanobacterial organism, or a selective growth medium, in a stable substrate form such as sodium alginate gel pellets and introducing the substrate into the environment to be sampled.

The method also has application for producing inoculum of pathogens, particularly viruses. This is accomplished by immobilizing a concentrated suspension of host cells, such as a host cyanobacterium, in alginate gel pellets. When the immobilized host cells are inoculated with a pathogen, the concentrated suspension of host cells then supports production of high concentrations of selected pathogens in the gel pellets. The pellets containing the pathogens can be easily harvested, used for storage of the pathogen, and/or formulated as inoculum.

In a preferred embodiment of the invention, cyanobacteria such as *Anabaena spp., Oscillatoria spp.*, or actimomycetes are used as target or host organisms to attract pathogenic microorganisms and/or viruses. The cyanobacterial target organisms are first grown in a laboratory shaker in submerged liquid culture. Pellets containing the target organisms are then prepared by dripping the submerged liquid culture containing 1% (w/v) sodium alginate mixture into a solution containing 0.25M $CaCl_2$. The pellets containing the target organisms are harvested from the $CaCl_2$ solution, rinsed in distilled water and pellets containing each type of target organism are placed in separate bags constructed from nylon window screen. Each bag is secured with monofilament fishing line and at least one bag and preferably multiple bags, typically from five to seven, linked together with monofilament fishing line, are placed in a sampling device.

The sampling device used in isolating microorganisms and viruses from an aquatic environment is typically characterized by a 1¼" diameter polyvinyl chloride (PVC) pipe which is approximately 12" long, sealed on one end and perforated with multiple openings. After the bags containing the gel pellets are placed in the sampling device, a cap is threaded on the open end of the sampling device, which is then placed in a carrying case filled with water or BG-11 growth medium. The carrying case is typically characterized by a 2" diameter PVC pipe which is approximately 14" long and sealed on one end. The other end is capped with a threaded plug after the sampling device is inserted.

The sampling procedure includes removing the sampling device from the carrying case and suspending the sampling device in a catfish pond or other body of water by means of a nylon cord which is attached to the end of the sampling device. After a selected period of time, typically from 2 to 7 days, the sampling device is retrieved from the body of water, again placed in the carrying case and transported to the laboratory for processing. The nylon bags are removed from the sampling device and the alginate gel pellets placed on cultures of an appropriate host organism growing in Petri dishes containing BG-11 growth medium solidified with agar. The cultures are incubated, typically in a Percival model I35-LLVL incubator at 28 degrees Centigrade. Twelve hours of diurnal light is provided by a combination of cool-white fluorescent lamps and fluorescent plant grow lamps. Development of plaques on the cyanobacterial cultures indicates the presence of lytic agents such as viruses, bacteria, fungi or substances released from the bacteria or fungi. The lytic agents are then transferred from the plaques to other cultures of the host organism for propagation and evaluation.

The following examples illustrate isolation of microorganisms and viruses from an aquatic environment using the method of this invention:

EXAMPLE 1

Preparation of Pellets Containing Target Organisms

Sodium alginate (1% final concentration of Kelgin MV) was added to separate cultures of the cyanobacteria *Anabaena spp., Oscillatoria spp.*, and actinomycetes, each grown on a laboratory shaker in submerged liquid culture. Pellets containing each cyanobacterium were prepared by dripping each mixture into a solution containing 0.25M $CaCl_2$. The pellets were then harvested from the $CaCl_2$ solution, rinsed in distilled water and pellets containing each type of target organism were placed in separate bags constructed from nylon window screen. A label was placed in each bag to indicate the target organism in the bag and each bag was sealed with monofilament fishing line. Five to seven bags, each containing a different target organism, were connected using monofilament fishing line and placed in one sampling device.

Construction of a Sampling Device

The sampling device was characterized by a 1¼" diameter polyvinylchloride (PVC) pipe which was approximately 12"

long, sealed on one end and perforated by drilling 75–100, ⅛" diameter holes along the length of the pipe. A 1¼" diameter cap was threaded on the open end of the perforated pipe and a nylon cord approximately 10 feet long was attached to the pipe, adjacent to the cap. The cord was wrapped around the pipe and the sampling device placed in a carrying case filled with water or BG-11 growth medium.

The carrying case used to carry the sampling device was characterized by a 2" diameter PVC pipe approximately 14" long, sealed on one end with a fixed cap and on the other end with a removable, threaded 2" diameter plug. After the carrying case was filled with water, (preferably distilled) or the BG-11 growth medium or an equivalent medium, the sampling device was placed in the carrying case, the threaded plug inserted and the sampling device was transported to a catfish pond.

The sampling procedure included removing the sampling device from the carrying case, unwinding the nylon cord and suspending the sampling device in the catfish pond using the nylon cord. After 5 days, the sampling device was retrieved from the catfish pond, again placed in the carrying case and transported to the laboratory for processing. The nylon bags were then removed from the sampling device and the pellets of each bag were placed in separate beakers containing BG-11 growth medium. The pellets from each beaker were placed on cultures of the corresponding target organism growing in Petri dishes containing BG-11 growth medium solidified with agar. These cultures were incubated in a Percival Model I35-LLVL incubator at 28° C. Twelve hours of diurnal light was provided by a combination of cool-white fluorescent lamps and fluorescent plant grow lamps. Development of plaques in the target organism cultures indicated the presence of lytic agents including bacteria, fungi and viruses. The lytic agents were transferred from the plaques to other cultures of the target organism for propagation and evaluation.

EXAMPLE 2

Using the procedure of Example 1, the target organisms were *Anabaena spp.*

EXAMPLE 3

Using the procedure of Example 1 and the target organisms of Example 2, the lytic agents isolated were viruses.

EXAMPLE 4

Using the procedure of Example 1 and the target organisms of Example 2, the lytic agents isolated were bacteria.

EXAMPLE 5

Using the procedure of Example 1 and the target organisms of Example 2, the lytic agents isolated were fungi.

EXAMPLE 6

Using the procedure of Example 1, the target organisms were *Oscillatoria spp.*

EXAMPLE 7

Using the procedure of Example 1, the target organisms were actinomycetes.

Additional applications of this procedure include isolating microorganisms or viruses that occur in low numbers from mixed populations of microorganisms or viruses, or isolation and detection of other types of pathogens such as water-borne pathogens of humans. The method of this invention may also be used to isolate microorganisms and/or viruses having selected properties from soil by immobilizing the host organisms or selective growth media in a stable substrate form, placing the substrate form in a bag or bags as described in Example 1, placing the bag or bags in a perforated sampling container such as a perforated canister, burying the sampling container in the soil for a selected period of time and isolating the microorganisms and/or viruses from the substrate form using the procedure described in Example 1 above. It is understood that other substrate forms such as vermiculite, corn cob grits, clay, or pellets prepared from Carrageenan, in nonexclusive particular, may be used instead of or, in addition to, sodium alginate gel pellets, to immobilize the host organisms or selective growth medium, according to the knowledge of those skilled in the art. It is further understood that the carrying case used to transport the sampling device and bags of pellets is filled with water or BG-11 growth medium to maintain the integrity of the pellets and/or target organisms. This procedure greatly enhances the efficiency of the sampling procedure.

While the preferred embodiments of the invention have been described above, it will be recognized and understood that various modification may be made in the invention and the appended claims are intended to cover all such modifications which may fall within the spirit and scope of the invention.

Having described my invention with the particularity set forth above, what is claimed is:

1. A method of isolating microorganisms and viruses from a water environment, comprising the steps of:
   immobilizing a target organism selected from the group consisting of gram-positive bacteria, gram-negative bacteria, *Oscillatoria spp.*, and *Anabeana spp.*, in a first stable substrate;
   placing said first stable substrate in a water environment for a selected period of time, whereby pathogens selected from the group consisting of microorganisms and viruses from the water environment which are pathogenic to said immobilized target organism colonize said target organism in said first stable substrate; and
   removing from the water environment said first stable substrate having said target organism immobilized therein, said target organism being colonized by said pathogens selected from the group consisting of microorganisms and viruses; thereby isolating said pathogens selected from the group consisting of microorganisms and viruses from said water environment.

2. The method of claim 1 wherein said first stable substrate is selected from the group consisting of sodium alginate gel pellets, vermiculite, corn cob grits, clay and pellets prepared from Carrageenan.

3. The method of claim 1 wherein said first stable substrate comprises a selective growth medium for said pathogens selected from the group consisting of microorganisms and viruses from the water environment.

4. The method of claim 3 wherein said selective growth medium comprises sodium alginate gel pellets.

5. A method of isolating viruses and microorganisms from an aquatic environment, comprising the steps of:
   immobilizing a concentrated suspension of target organisms in sodium alginate gel pellets;
   placing said pellets in at least one perforated bag;
   sealing said bag and placing said bag in a perforated sampling device;

suspending said sampling device in a body of water for a selected period of time, whereby pathogens selected from the group consisting of viruses and microorganisms from the body of water which are pathogenic to said immobilized target organisms colonize said target organisms in said pellets;

removing said sampling device from said body of water;

removing said at least one perforated bag from said sampling device; and removing said pellets from said at least one perforated bag, thereby isolating said pathogens selected from the group consisting of viruses and microorganisms from said body of water.

6. The method of claim 5 wherein said target organisms include *Oscillatoria spp.*

7. The method of claim 5 wherein said target organisms include actinomycetes.

8. The method of claim 5 wherein said target organisms include *Anabaena spp.*

9. The method of claim 1 further comprising the steps of:

removing said pathogens selected from the group consisting of microorganisms and viruses which are pathogenic to said immobilized target organism from said first stable substrate; and immobilizing a concentrated suspension of host cells in a second stable substrate and inoculating said host cells with said pathogens selected from the group consisting of microorganisms and viruses which are pathogenic to said immobilized target organism for propagating said pathogens selected from the group consisting of microorganisms and viruses which are pathogenic to said immobilized target organism that are available for additional inoculation.

10. A method of claim 9 wherein said host cells are selected from the group consisting of cyanobacteria, actinomycetes and fungi.

* * * * *